US006358542B2

(12) United States Patent
Cuomo et al.

(10) Patent No.: US 6,358,542 B2
(45) Date of Patent: Mar. 19, 2002

(54) ANTIOXIDANT COMPOSITIONS EXTRACTED FROM OLIVES AND OLIVE BY-PRODUCTS

(75) Inventors: John Cuomo; Alexandre B. Rabovskiy, both of Salt Lake City, UT (US)

(73) Assignee: Usana, Inc., Salt Lake City, UT (US)

( * ) Notice: Subject to any disclaimer, the term of this patent is extended or adjusted under 35 U.S.C. 154(b) by 0 days.

(21) Appl. No.: 09/467,439

(22) Filed: Dec. 20, 1999

(51) Int. Cl.$^7$ ................. A61N 35/78; A61N 39/385; A01N 65/00

(52) U.S. Cl. ..................... 424/777; 424/725

(58) Field of Search ............... 426/541, 542, 426/49, 546; 424/195.1, 725, 777

(56) References Cited

U.S. PATENT DOCUMENTS

| 4,297,220 A | | 10/1981 | Meitzner et al. |
| 5,132,294 A | * | 7/1992 | Mimura et al. |
| 5,714,150 A | | 2/1998 | Nachman |
| 5,939,395 A | * | 8/1999 | Yu et al. |

FOREIGN PATENT DOCUMENTS

EP 811678 12/1997

OTHER PUBLICATIONS

Litridou et al., J of the Science of Food & Agriculture, vol. 72(2): 169–172. Phenolic compounds in virgin olive oils: Fractionation by solid phase extraction and antioxidant activity assessment, Jun. 1997.*

Servili et al., J Am Oil Chemists' Soc., vol. 76(7): 873–882. High performance liquid chromatography evaluation of phenols in olive fruit, virgin olive oil, vegetation waters, and pomace and 1D– and 2D nuclear magnetic resonance characterization, Jul. 1999.*

Antonio Trichopoulou, Klea Katsouyanni, Sherri Stuver, Lia Tzala, Charalambos Gnardellis, Eric Rimm, Dimitros Trichopoulos, "Consumption of Olive Oil and Specific Food Groups in Relation to Breast Cancer Risk in Greece," Journal of the National Cancer Institute, vol. 87, No. 2, Jan. 18, 1995, pp. 110–116.

F. Visioli and C. Galli, "Natural Antioxidants and Prevention of Coronary Heart Disease: The Potential Role of Olive Oil and Its Minor Constituents," Nutr Metab Cardiovasc Dis (1995) 5:306–314.

Walter C. Willet, Frank Sacks, Antonio Trichopoulou, Greg Drescher, Anna Ferro–Luzzi, Elisabet Helsing, and Dimitros Trichopoulos, "Mediterranean Diet Pyramid: A Cultural Model for Healthy Eating," Am J Clin Nutr 1995; 61(suppl):1402S–1406S.

A. Petroni, M. Blasevich, M. Salami, M. Servilli, G.F. Montedoro, C. Galli, "A Phenolic Antioxidant Extracted from Olive Oil Inhibits Platelet Aggregation and Arachidonic Acid Metabolism in Vitro," World Rev Nutr Diet, Basel, Karger, 1994, vol. 75, pp. 169–172.

Caterina Manna, Patrizia Galleti, Valeria Cucciolla, Ornella Moltedo, Arturo Leone and Vincenzo Zappia "The Protective Effect of the Olive Oil Polyphenol (3,4–Dihydroxyphenyl)–Ethanol Counteracts Reactive Oxygen Metabolite–Induced Cytotoxicity in Caco–2 Cells," J. Nutr. 1997; 127:286–292.

Francesco Visioli, Giorgio Bellomo, GianFranco Montedoro, Claudio Galli, "Low Density Lipoprotein Oxidation is Inhibited in Vitro by Olive Oil Constituents," Atherosclerosis 117 (1995), pp. 25–32.

F. Visioli, F.F. Vinceri and C. Galli, "Waste Waters' from Olive Oil Production are Rich in Natural Antioxidants," Experientia, 1995; 51:32–34.

C. Scaccini, M. Nardini, M.D' Aquino, V. Gentili, M. Di Felice, and G. Tomassi, "Effect of Dietary Oils on Lipid Peroxidation and on Antioxidant Parameters of Rat Plasma and Lipoprotein Fractions," Journal of Lipid Research, vol. 33, 1992, pp. 627–633.

Jose M. Martin–Moreno, Walter C. Willett, Lydia Gorgojo, Jose R. Banegas, Fernando Rodriguez–Artalejo, Juan C. Fernandez–Rodriguez, Patrick Maisonneuve and Peter Boyle, "Dietary Fat, Olive Oil Intake and Breast Cancer Risk," Int J. Cancer (1994) 58:774–780.

Sheila A. Wiseman, Jolanda N.N.J. Mathot, Nanneke J. de Fouw, Lilian B.M. Tijburg, "Dietary Non–Tocopherol Antioxidants Present in Extra Virgin Olive Oil Increase the Resistance of Low Density Lipoproteins to Oxidation in Rabbits," Atheroslcerosis 120 (1996), pp. 15–23.

(List continued on next page.)

*Primary Examiner*—Christopher R. Tate
*Assistant Examiner*—Michele C. Flood
(74) *Attorney, Agent, or Firm*—Workman, Nydegger & Seeley

(57) ABSTRACT

The present invention provides methods of extracting antioxidant compositions from olive-based starting materials, including olives, olive pulps, olive oil, and wastewater from olive oil manufacturing. One method includes the steps of extracting the olives, olive pulp or olive oil with a polar aqueous solvent to form an aqueous phase containing antioxidant components, passing the aqueous phase through a solid matrix to trap the antioxidant components on the matrix, and washing the matrix with a polar organic solvent to yield a solution of the antioxidant composition in the polar organic solvent. Another method includes the steps passing the wastewater from olive oil production containing antioxidant components through a solid matrix to trap the antioxidant components on the matrix, and washing the matrix with a polar organic solvent to yield a solution of the antioxidant composition in the polar organic solvent. The present invention also provides antioxidant compositions and methods of increasing the antioxidant activity of a product using such compositions.

42 Claims, 6 Drawing Sheets

OTHER PUBLICATIONS

Francesco Visioli, Giorgio Bellomo, and Claudia Galli, "Free Radical–Scavenging Properties of Olive Oil Polyphenols," Biochemical and Biophysical Research Communications (1998) 247:60–64.

Francesco Visioli and Claudio Galli, "Olive Oil Phenols and Their Potential Effects on Human Health," J. Agric. Food Chem., 1998, vol. 46, No. 10, pp. 4292–4296.

Gerd Assmann, et al., "Olive Oil and the Mediterranean Diet: Implications for Health in Europe," British Journal of Nursing, 1997, vol. 6, No. 12, pp. 675–677.

Michel de Lorgeril, MD, Patricia Salen, BSc., Jean–Louis Martin, Ph.D., Isabelle Monjaud, BSc., Philippe Boucher, PhD., Nicole Mamelle, PhD., "Mediterranean Dietary Pattern in a Randomized Trial," Arch Intern. Med., vol. 158, Jun. 8, 1998, pp. 1181–1187.

Mario Mancini, MD., Vernon J. Parfitt, MD., Paolo Rubbs, MD., "Antioxidants in the Mediterranean Diet," Can J Cardiol, vol. 11, Suppl. G, Oct. 1995, pp. 105G–109G.

Ma. M. Rodriguez, J. Perez, A. Ramos–Cormenzana & J. Martinez, "Effect of Extracts Obtained from Olive Oil Mill Waste Waters on *Bacillus Megaterium* ATCC 33085," Journal of Applied Bacteriology 1988, 64:219–225.

J. Perez, T. de la Rubia, J. Moreno and J. Martinez, "Phenolic Content and Antibacterial Activity of Olive Oil Waste Waters," Environmental Toxicology and Chemistry, vol. 11, pp. 489–495, 1992.

Francesco Visioli and Claudio Galli, "Oleuropein Protects Low Density Lipoprotein from Oxidation," Lif Sciences, 1994, vol. 55, No. 24, pp. 1965–1972.

H.S. Tranter, Soula C. Tassou and G.J. Nychas, "The Effect of the Olive Phenolic Compound, Oleuropein, on Growth and Enterotoxin B Production by *Staphylococcus Aureus*," Journal of Applied Bacteriology, 1993, 74:253–259.

Satoshi Tamai, Miyuki Kaneda and Shoshiro Nakamura, "Piperazinomycin, a New Antifungal Antibiotic," The Journal of Antibiotics, Sep. 1982, vol. 35, No. 9, pp. 1130–1136.

B. Gawdzik, J. Gawdzik and U. Czerwinska–Bil, "Use of Polymeric Sorbents for the Off–Line Preconcentration of Prioity Pollutant Phenols from Water for High–Performance Liquid Chromatographic Analysis," Journal of Chromatography, 509 (1990), pp. 135–140.

B. Juven and Y. Henis, "Studies on the Antimicrobial Activity of Olive Phenolic Compounds," J. Appl. Bact, 1970, 33:721–732.

C.C. Tassou and G.J.E. Nychas, "Inhibition of *Salmonella Enteritidis* by Oleuropein in Broth and in a Model Food System," Letters in Applied Microbiology, 1995, 20:120–124.

Noriko Kohyama, Tadahiro Nagatak, Shin–ichi Fujimoto and Keizo Sekiya, "Inhibition of Arachidonate Lipoxygenase Activities by 2–(3,4–Dihydroxyphenyl)ethanol, a Phenolic Compound from Olives," Biosci. Biotech. Biochem., 1997 61(2):347–350.

N. Masque, M. Galia, R.M. Marce and F. Borrull, "Solid–Phase Extraction of Phenois and Pesticides in Water with a Modified Polymeric Resin," Analyst, May 1997, vol. 122, pp. 425–428.

Michel Dubois, K.A. Gilles, J.K. Hamilton, P.A. Rebers and Fred Smith, "Colorimetric Method for Determination of Sugars and Related Substances," Analytical Chemistry, vol. 28, No. 3, Mar. 1956, pp. 350–356.

H.P. Fleming, W.M. Walter, Jr. and J.L. Etchells, "Antimicrobial Properties of Oleuropein and Products of Its Hydrolysis from Green Olives," Applied Microbiology, Nov. 1973, vol. 26, No. 5, pp. 777–782.

Igor N. Popov, Gudrun Lewin, "Photochemiluminescent Detection of Antiradical Activity; IV: Testing of Lipid–Soluble Antioxidants," J. Biochem. Biophys. Methods 31 (1996), pp. 1–8.

A.L.E. Mahmoud, "Antifungal Action and Antiaflatoxigenic Properties of Some Essential Oil Constituents," Letters in Applied Microbiology, 1994, 19:110–113.

Rohm and Haas Brochure, Ion Exchange Resins, "Ambertlite® XAD7HP Polymeric Absorbent," Jan., 1999.

Rohm and Haas Brochure, Ion Exchange Resins, "Amberlite® XAD Polymeric Absorbents," Jan., 1999.

Rohm and Haas Brochure, Ion Exchange Resins, "Amberlite® and Duolite® Polymeric Absorbents", May, 1991.

Rohm and Haas Brochure, Ion Exchange Resins, "Amberlite® XAD–16 Polymeric Absorbents," Jun., 1993.

Rohm and Haas Brochure, Ion Exchange Resins, "Amberlite® XAD–1180 Polymeric Absorbents," Jun., 1993.

Anna Petroni, Milena Blasevich, Marco Salami, Nadia Papini, Gian F. Montedoro and Claudio Galli, "Inhibition of Platelet Aggregation and Eicosaniod Production by Phenolic Components of Olive Oil," Thrombosis Research, vol. 78, No. 2, pp. 151–160, 1995.

Anna Petroni, Milena Blasevich, Nadia Papini, Marco Salami, Angelo Sala and Claudio Galli, "Inhibition of Leukocyte Leukotriene $B_4$ Production by an Olive–Derived Phenol Identified by Mass–Spectrometry," Thrombosis Research, vol. 87, No. 3, pp. 315–322, 1997.

H. Esterbauer, G. Striegl, H. Puhl and M. Rotheneder, "Continuous Monitoring of In Vitro Oxidation of Human Low Density Lipoprotein," Free Rad. Res. Commms., vol. 6, No. 1, pp. 67–75, 1989.

Katerina Pattichis, Louis L. Louca, Joan Jarman, Merton Sandler, Vivette Glover, "5–Hydroxytryptamine Release from Platelets by Different Red Wines: Implications for Migraine," European Journal of Pharmacology, Environmental Toxicology and Pharmacology Section 292, Jan. 13, 1995, pp. 173–177.

R. Aeschbach, J. Loliger, B.C. Scott, A. Murcia, J. Butler, B. Halliwell and O.I. Aruoma, "Antioxidant Actions of Thymiol, Carvocrol, 6–Gingerol, Zingerone and Hydroxytyrosol," Food Chem. Toxic., vol. 32, No. 1, pp. 31–36, Jan., 1994.

Michel de Lorgeril, M.D., Patricia Salen, BSc., Jean–Louis Martin, PhD., Isabelle Monjaud, BSc., Philippe Boucher, PhD., Nicolle Mamelle, PhD., "Mediterranean Dietary Pattern in a Randomized Trial: Prolonged Survival and Possible Reduced Cancer Rate," Arch. Intern. Med., vol. 158, Jun. 8, 1998, pp. 1181–1187.

A. Ghiselli, A. D'Amicis and A. Glacosa, "The Antioxidant Potential of the Mediterranean Diet," European Journal of Cancer Prevention, vol. 6 (Supp.1), pp. S15–S19, Mar. 1997.

V.L. Singleton and Joseph A. Rossi, Jr., "Colorimetry of Total Phenolics With Phosphomolybdic–Phosphotungstic Acid Reagents," American Journal of Enology and Viticulture, vol. 16, No. 3, pp. 144–158, 1965.

* cited by examiner

ANTIOXIDANT COMPOSITIONS EXTRACTED FROM OLIVES AND OLIVE BY-PRODUCTS

FIELD OF THE INVENTION

The present invention relates to methods of extracting anti-oxidant compositions from olives and the by-products of olive oil production. More specifically, the present invention provides simple and efficient methods of obtaining compositions rich in antioxidant compounds from fresh olives, from olive pulps produced as a by-product of olive oil manufacturing, from olive oil, and from wastewater from olive oil manufacturing. The invention also relates to anti-oxidant compositions and products containing the antioxidant compositions.

BACKGROUND

The Mediterranean diet, a diet rich in fresh fruits, vegetables and relatively low in animal fats, has long been considered exemplary of healthy diets. Part of the perceived health benefits of the Mediterranean diet has been attributed to the consumption of olive oil as the principal dietary fat. (See, e.g., Willett, W., Sacks, F., Trichopoulou, A., Drescher, G., Ferro-Luzzi, A., Helsing, E., Trichopoulos, D., "Mediterranean diet pyramid: a cultural model for healthy eating", Am. J. Clin. Nutr., 1995; 61(suppl): 1402S–1406S.) Indeed, consumption of olive oil has been shown to be associated with a variety of health benefits, including a lower incidence of heart disease and a lower incidence of breast cancer. Visioli, F., Galli, C., "Natural antioxidants and prevention of coronary heart disease: the potential role of olive oil and its minor constituents", Nut. Metab. Cardiovasc. Dis., 1995; 5: 306–314, and Trichopoulou, A., Katsouyanni, K., Stuver, S., Tzala, L., Gnardellis, C., Rimm, E. and Trichopoulos, D., "Consumption of Olive Oil and Specific Food Groups in Relation to Breast Cancer Risk in Greece", J. Nat. Cancer Inst., 1995; 87(2): 110–116. These findings have prompted considerable research into the composition of olive oil, and the nature of the components of olive oil responsible for the observed beneficial health effects.

Much of the benefit of olive oil consumption has been attributed to the presence of natural antioxidant compounds, several of which have been isolated. Among the antioxidant compounds that have been isolated from olive oil are various phenolic compounds, including hydroxytyrosol ((3,4-dihydroxyphenyl)ethanol), tyrosol (p-hydroxyphenylethanol), p-hydroxybenzoic acid, vanillic acid, caffeic acid, oleuropein and other phenolic compounds. The structures of several of these phenolic compounds are shown for reference.

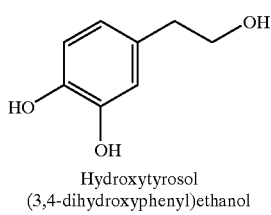

Hydroxytyrosol
(3,4-dihydroxyphenyl)ethanol

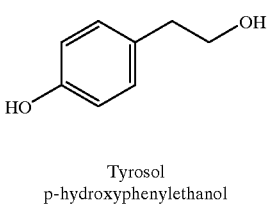

Tyrosol
p-hydroxyphenylethanol

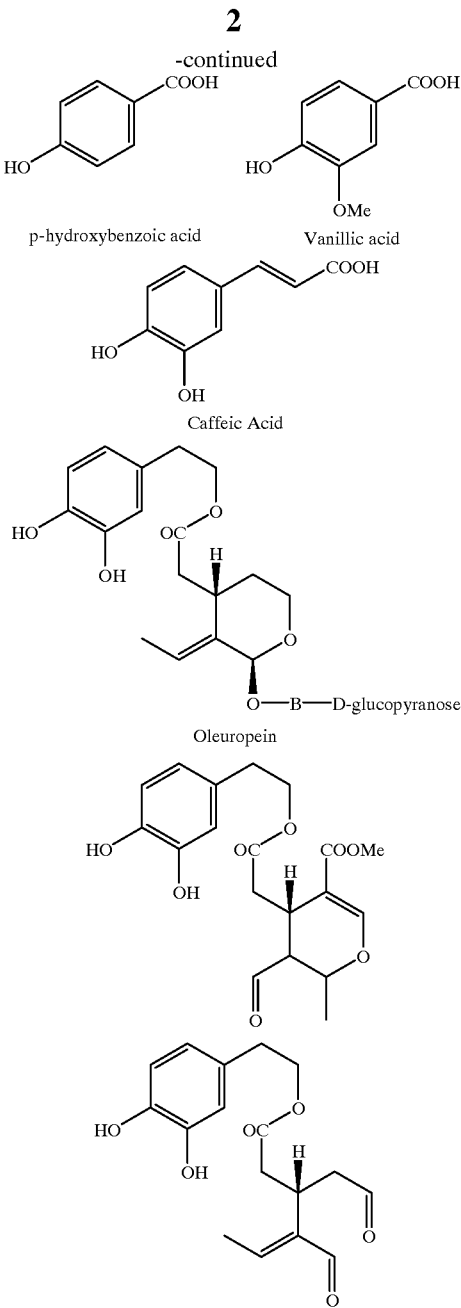

These compounds have shown in vitro biological activity, including inhibition of platelet aggregation (Petroni, A., Blasevich, M., Salami, M., Papini, N., Montedoro, G. F., Galli, C., "Inhibition of platelet aggregation and eicosanoid production by phenolic components of olive oil", Thrombosis Research, 1995; 78: 151–160), inhibition of LDL oxidation Visioli, F., Bellomo, G., Montedoro, G., Galli, C., "Low density lipoprotein oxidation is inhibited in vitro by olive oil constituents", Atherosclerosis, 1995; 117: 25–32), prevention of reactive oxygen metabolite (ROM)-induced cytotoxicity in human cell culture (Manna, C., Galletti, P., Cucciolla, V., Moltedo, O., Leone, A., Zappia, V., "The Protective Effect of the Olive Oil Polyphenol (3,4-Dihydroxyphenyl)ethanol Counteracts Reactive Oxygen Metabolite-Induced Cytotoxicity in Caco-2 Cells", J. Nutr., 1997; 127: 286–292), inhibition of formation of thromboxane $B_2$ ($TxB_2$) (Petroni, A., Blasevich, M., Salami, M., Servili, M., Montedoro, G. F., Galli, C., "A Phenolic Antioxidant Extracted from Olive Oil Inhibits Platlet Aggregation and Arachidonic Acid Metabolism in vitro", *World Rev. Nutr. Diet,* 1994; 75: 169–172), and inhibition of formation of leukotriene $B_4$ (LTB$_4$) (Petroni, A., Blasevich, M., Papini, N., Salami, M., Sala, A., Galli, C, Inhibition of leukocyte leukotriene $B_4$ production by an olive oil-derived phenol identified by mass-spectrometry", *Thrombosis Research,* 1997; 87: 315–322). Thromboxane $B_2$ and leukotriene $B_4$ are two important substances secreted by polymorphonuclear leukocytes involved in pathophysiological processes related to chronic inflammation and vascular injury. In addition, phenolic compounds in olive oil have shown antibiotic activity with both antimicrobial (see, e.g., Juven, B., Henis,Y., "Studies on the antimicrobial activity of olive phenolic compounds", *J. Appl. Bacteriol,* 1970; 33: 721–732) and antifungal properties (Mahmoud, A. L., "Antifungal action and antiaflatoxigenic properties of some essential oil constituents", *Lett. Appl. Microbiol.,* 1994; 19: 110–113). Moreover, animal studies have shown that LDL from olive oil-fed rodents is significantly more resistant to oxidation than control samples (Scaccini, C., Nardini, M., D'Aquino, M., Gentili, V., Di Felice, M., Tomassi, G., "Effect of dietary oils on lipid peroxidation and on antioxidant parameters of rat plasma and lipoprotein fractions", *J. Lipid Res.,* 1992; 33: 627–633). Thus, in light of the increasing amount of evidence showing the potential health benefits of olive oil and components of olive oil, it would be desirable to have processes for extracting antioxidant components from olive oil.

Despite the need for olive-derived antioxidant compositions, the prior art does not provide simple and effective processes for producing such compositions. European Patent Application No. EP 0 811 678 A1 discloses a process for extracting antioxidants from olives, in which olives are crushed, vacuum dried, and pressed to form a cake. The cake is then extracted with a hot medium chain triglyceride or a $C_2$ to $C_6$ alkylene glycol at a pressure of at least 40 bar, to obtain an antioxidant-enriched extract. This method requires the use of a pressure-piston apparatus for extraction, lyophilization equipment and supplies for freeze-drying, and other equipment and chemicals that result in a relatively complex, expensive process. Moreover, this process uses fresh green or ripe olives, which can be expensive.

Olive oil production, which also uses fresh olives, produces as by-products a solid olive mass, often called "pulp", and wastewater from a water-olive slurry conventionally used in olive oil manufacturing. These olive oil production by-products, are potentially rich in antioxidant compounds, but have not been effectively exploited, due to the impracticality of extracting usable amounts of antioxidant compounds using conventional technology. Indeed, although it has been reported that olive oil production wastewater is rich in phenolic antioxidant compounds (Visioli, F., Vinceri, F. F., Galli, C., "Waste waters from olive oil production are rich in natural antioxidants", *Experientia,* 1995; 51: 32–34), there still does not exist a simple and practical method of extracting such compounds from the wastewater. In addition, several inferior grades of olive oil now used in industrial (rather than culinary) applications, and therefore relatively inexpensive compared to culinary grade olive oil, offer potentially rich sources of antioxidant compounds. To date, however, these potential sources of beneficial antioxidants have not been effectively exploited.

Thus, there is a need for methods of obtaining antioxidant compositions from olives, olive oil and olive oil manufacturing by-products that do not suffer from the foregoing disadvantages.

SUMMARY OF THE INVENTION

It is an object of the invention to provide cheaper and more effective methods of extracting antioxidant compositions from olives.

It is another object of the invention to provide methods of extracting antioxidant compositions from olive oil.

It is another object of the invention to provide methods of using olive pulp by-products of olive oil manufacturing to produce antioxidant compositions.

It is another object of the invention to provide methods of using wastewater from olive oil manufacturing to produce antioxidant compositions.

It is another object of the invention to provide naturally-derived compositions rich in antioxidant components.

It is still another object of the invention to provide antioxidant compositions that can be used to impart antioxidant activity to, or enhance the antioxidant activity in, products such as cosmetics, topical antioxidant compositions, nutritional supplements, food products, oils or preservative compositions.

In accordance with these and other objects, the present invention provides methods of extracting antioxidant compositions from various olive-based starting materials, such as green olives, black olives, olive pulps, olive oil, and wastewater from olive oil manufacturing. The present invention further provides antioxidant compositions produced by the present methods, as well as methods of enhancing the antioxidant activity of a product.

In one embodiment, the present invention provides a method of preparing an antioxidant composition from an olive, an olive pulp, or an olive oil. The method includes the steps of extracting the starting material with a polar aqueous solvent to form an aqueous phase containing antioxidant components, passing the aqueous phase through a solid matrix to trap the antioxidant components on the matrix, and washing the matrix with a polar organic solvent to yield a solution of the antioxidant composition in the polar organic solvent. Optionally, the organic solvent can be partially removed to form a liquid concentrate, or further removed to leave a dry, solid antioxidant composition.

In another embodiment, the present invention provides a method of preparing an antioxidant composition from wastewater from olive oil manufacturing. The method includes the steps passing the wastewater containing antioxidant components through a solid matrix to trap the antioxidant components on the matrix, and washing the matrix with a polar organic solvent to yield a solution of the antioxidant composition in the polar organic solvent. Optionally, the organic solvent can be partially removed to form a liquid concentrate, or further removed to leave a dry, solid antioxidant composition.

In another embodiment, the present invention provides an antioxidant composition produced by any of the methods of the present invention.

In another embodiment, the present invention provides nutritional supplements having antioxidant activity and including an antioxidant composition produced by any of the methods of the present invention.

In another embodiment, the present invention provides a method of increasing the antioxidant activity of a product. The method includes the steps of obtaining an antioxidant composition from olives, olive pulp, olive oil, or wastewater from olive oil production, and combining the antioxidant composition with a product to enhance the antioxidant activity of the product.

These and other objects and features of the present invention will become more fully apparent from the following description and appended claims, or may be learned by the practice of the invention as set forth hereinafter.

BRIEF DESCRIPTION OF THE DRAWINGS

In order to illustrate the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1A:
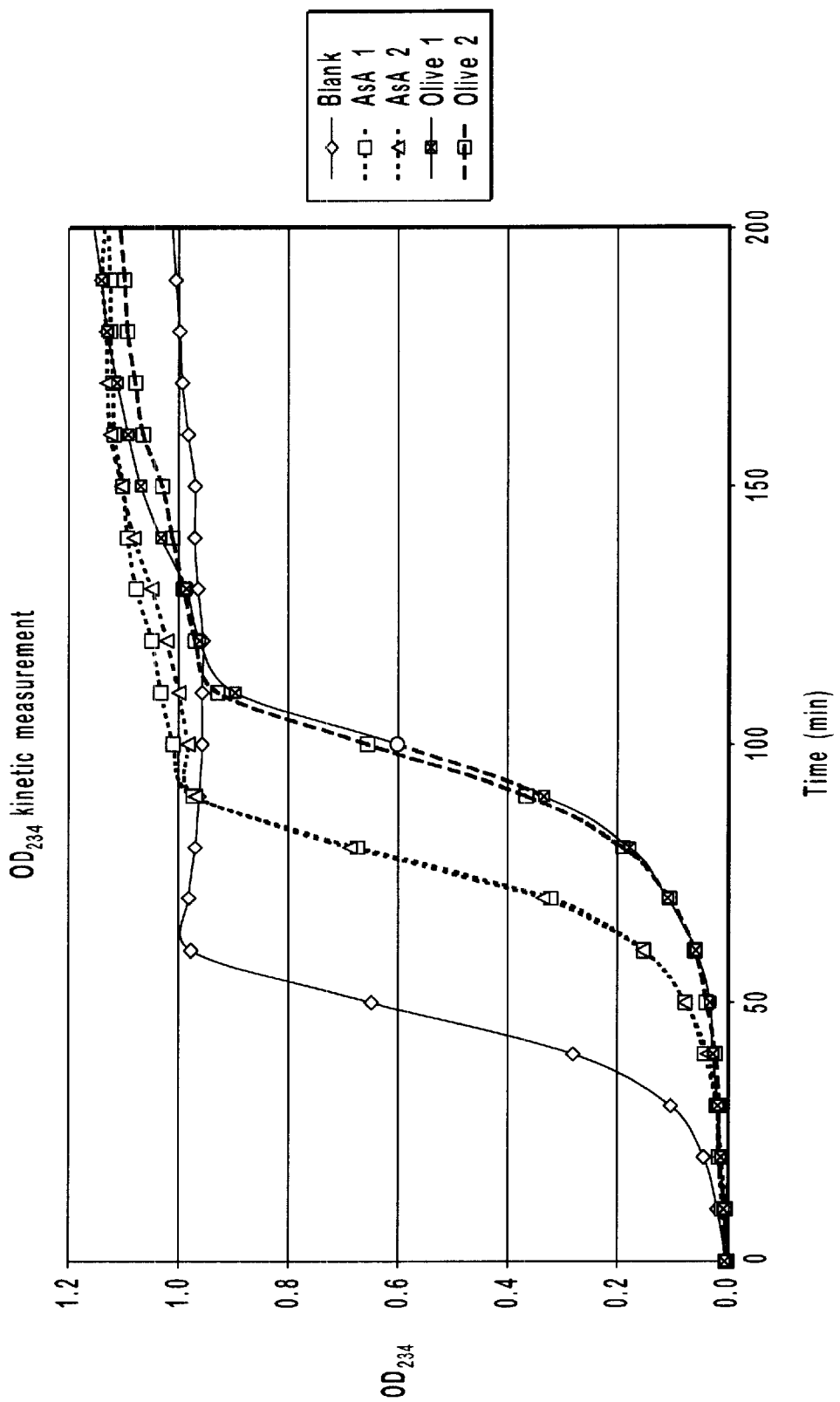
FIG. 1A shows the kinetics of conjugated diene formation in human LDL by measurement of optical density versus time.

The present invention provides methods of extracting antioxidant compositions from olive-based starting materials, such as olives, olive pulps, olive oil, and wastewater from olive oil manufacturing. The methods simply and efficiently extract beneficial antioxidants from the starting material, providing antioxidant compositions that can be used in a variety of ways to provide beneficial antioxidant activity to a product, or to enhance the antioxidant activity of a product. It has been surprisingly discovered that the methods of the present invention can extract beneficial antioxidant compositions from a wide variety of olive-based starting materials, including the by-products of olive oil production that would otherwise present waste disposal problems.

In one embodiment, the present invention provides a method of preparing an antioxidant composition from an olive, an olive pulp, or an olive oil. The method includes the steps of extracting the starting material with a polar aqueous solvent to form an aqueous phase containing antioxidant components, passing the aqueous phase through a solid matrix to trap the antioxidant components on the matrix, and washing the matrix with a polar organic solvent to yield a solution of the antioxidant composition in the polar organic solvent.

In one step, the method includes providing an olive-based starting material. The starting material can be any of a wide variety of olive-based materials that contain at least some antioxidant compounds. The starting material can be the olive fruit, including green olives, black (ripe) olives, olives in intermediate stages of ripeness, olives that are over-ripe, or mixtures thereof. Such olives can be whole olives, or a crushed or ground olive material. The olives can be fresh or partially or completely dried.

Alternatively, the starting material can be the pulp from olive oil manufacturing. In a conventional olive oil manufacturing process, olive fruit, with or without pits, is ground, milled or crushed into a slurry or paste containing the crushed olive material, water, and olive oil. The slurry is then extruded into a press, which is typically a hydraulic press or a centrifugal press, where the liquid components are separated from the solids. The solids are referred to by some manufacturers as a "pulp", and by other manufacturers as a "cake"0 or "mash". Moreover, the solids can have varying degrees of water and oil content, depending upon the manufacturer and the specific manufacturing techniques used. For purposes of the present invention, any of these materials can be used, and the term "pulp"0 is used to refer to any of these olive pulps, mashes or cakes.

The starting material can also be an olive oil, without regard to the purity or grade of the oil. The oil can be any of the olive oils typically sold to consumers for culinary uses, or industrial grade olive oil typically manufactured from olive pulp or inferior olives for industrial uses, such as soap-making.

Mixtures of any of the olive-based starting materials can also be used in the methods of the present invention.

In another step, the starting material is extracted with a polar aqueous solvent to form an aqueous phase containing antioxidant components extracted from the starting material. The extraction step can be carried out in any convenient fashion known to those skilled in the art. Preferably, when the starting material includes olives, the olives are pitted and crushed, chopped, ground, or subjected to any other process to produce a plurality of olive particles. The starting material is then mixed with the polar aqueous solvent, whereby at least a portion of the antioxidant components contained in the starting material will be partitioned in the aqueous phase. The polar aqueous solvent can be water, or a mixture of water and any polar solvent that is water miscible, such as a water-miscible polar organic solvent. Suitable water-miscible polar organic solvents include $C_1$ to $C_4$ alcohols, esters, amides, ethers, nitrites and ketones. Preferred water-miscible organic solvents include $C_1$ to $C_4$ alcohols, particularly methanol, ethanol, propanol and isopropanol; acetone; dimethyl sulfoxide; dioxane; acetonitrile; DMF; and mixtures thereof. Most preferably, the polar aqueous solvent is a mixture of water and methanol, ethanol, acetonitrile, or acetone.

The extraction can be carried out at any convenient temperature. It will be apparent to those skilled in the art that more efficient extraction will occur if the mixture of the starting material is agitated, such as by stirring or shaking, and/or if the mixture is heated. In a preferred embodiment, the mixture is heated to the reflux temperature, and allowed to reflux, with stirring, for about one hour. However, any temperature between about room temperature (i.e., about 20° C.) and the reflux temperature may be used, and the extraction time can be only a few seconds, or several hours or days. Lower extraction temperatures, such as those below room temperature, can be used, but are not preferred. Longer extraction times can also be used, but it is presently believed that an extraction time of about one hour at the reflux temperature offers the best balance of time versus efficiency.

After the extraction is finished, the mixture will separate into at least two phases. Thus, when the starting material includes solid material, the mixture will separate at least into a solid phase and an aqueous phase, and generally into a solid phase, an oil phase, and an aqueous phase. When the starting material is olive oil, the mixture will separate into an oil phase and an aqueous phase. In either case, the aqueous phase is removed, such as by simple decantation, and the remaining phases discarded. Alternatively, the oil and/or solid phases can be extracted again with the same or a different polar aqueous solvent, and the aqueous phase from this second extraction also treated in accordance with the present method, preferably by combining with the aqueous phase from the first extraction. It should be appreciated that still further extractions of the solid and/or oil phases can be used, if desired.

In a preferred aspect of the present method, the polar aqueous solvent further includes an acid that is soluble in the polar aqueous solvent and present in an amount such that the polar aqueous solvent has an acidic pH. Without wishing to be bound by theory, it is believed that a significant amount of the antioxidant activity of the compositions of the present invention is due to phenolic antioxidants that are sufficiently polar to be efficiently partitioned into the polar aqueous phase. Among the phenolic antioxidants believed to be present in the starting material are hydrolyzable antioxidants, such as oleuropein. Thus, it is believed that extraction efficiency is improved by extracting the starting material in an acidic polar aqueous solvent. Preferably, the acidic polar aqueous solvent has a pH of about 0 to about 4, more preferably about 1 to about 3. Suitable acids include hydrochloric acid, sulfuric acid, phosphoric acid, and other conventional acids.

Optionally, the aqueous phase can be distilled to remove any organic solvents.

In another step of the present method, the antioxidant components in the aqueous phase are concentrated, preferably until a solid antioxidant composition is formed. The aqueous phase can be concentrated by allowing the polar aqueous solvent to evaporate, or by extracting the polar aqueous solvent with an organic solvent, such as ethyl acetate. However, it has been surprisingly found that the antioxidant components of the aqueous phase can be separated from the aqueous phase and concentrated using a solid matrix, and the use of a solid matrix is particularly preferred.

The solid matrix can be any material having a stronger affinity for at least some of the antioxidant components than for the aqueous phase. The solid matrix is preferably composed of a plurality of small particles having a large surface area, such as chromatographic beads. Preferably, the solid matrix is a solid phase resin, and is disposed in a bed or a chromatographic column.

A particularly preferred solid matrix material is a polymeric adsorbent material commercially available from Rohm and Haas and marketed under the trademark AMBERLITE®. The AMBERLITE® material is a macroreticulated crosslinked copolymer having a plurality of microscopic channels resulting from the liquid expulsion of a precipitating agent during polymerization of a monomer mixture under suspension conditions. These resins are typically styrenic, acrylic, or phenolic-based, and are described in more detail in U.S. Pat. No. 4,297,220, the disclosure of which is incorporated herein by reference in its entirety. Among the AMBERLITE® resins, polystyrene-based resins are preferred. Preferred resins include AMBERLITE® XAD-2, AMBERLITE® XAD-4, AMBERLITE® XAD-7 and AMBERLITE®0 XAD-16. Also preferred are other polystyrene resins, such as DUOLITE®, particularly DUOLITE® S-761.

The aqueous phase is passed over the solid matrix material, conveniently in a bed or a column. At least a portion of the antioxidant components in the aqueous phase preferentially adheres to the solid matrix material, while the remaining aqueous phase, at least partially depleted of antioxidant compounds, passes through the solid matrix material. Optionally, the at least partially depleted aqueous phase can be passed over solid matrix material in second, third or more repetitions.

In another step of the present method, the adsorbed antioxidant components are removed from the solid matrix material by washing the matrix with a solvent having a stronger affinity for at least some of the antioxidant components than the affinity of the solid matrix material for the antioxidant components. Suitable solvents include polar organic solvents, or aqueous mixtures of polar organic solvents, particularly $C_1$ to $C_4$ alcohols, acetone, ethyl acetate, acetonitrile, dioxane, and mixtures thereof The eluted solution is a solution of the antioxidant composition in the polar organic solvent.

Optionally and preferably, the antioxidant composition solution is concentrated by removing at least a portion of the polar organic solvent. To form a liquid concentrate, a desired portion of the polar organic solvent can be removed. In a most preferred embodiment, substantially all of the polar organic solvent is removed, to leave a solid antioxidant composition. The polar organic solvent can be removed by conventional means, such as by evaporation.

As described above in connection with the extraction step, the antioxidant activity of the composition can be enhanced by treating the composition with an acid. Thus, an optional step is to acidify the solution of the antioxidant composition in the polar organic solvent, by adding an acid miscible therein in an amount sufficient to give the solution an acidic pH, preferably a pH of about 0 to about 4, and more preferably about 1 to about 3. Alternatively, the solid antioxidant composition formed by evaporation of the polar organic solvent can be dissolved in an acidic solvent of pH about 0 to about 4, preferably about 1 to about 3, then re-concentrated by removing the acidic solvent. Thus, the optional step of acid treatment can be carried out at the extraction stage, as described above, or after the antioxidant composition has been washed from the solid matrix material, before or after evaporation or partial evaporation of the polar organic solvent. It is preferred that the acid treatment be performed only once, as it is not presently believed that performing the acid treatment a second or third time provides a significant benefit. In the most preferred embodiments, either the acid is provided in the polar aqueous solvent extraction, or the solid antioxidant composition is dissolved in an acidic solvent, which is subsequently removed.

The present invention also provides antioxidant compositions produced by the above-described method. In a preferred aspect, the antioxidant compositions are solid compositions. In another preferred aspect, the antioxidant compositions are liquid concentrates in the polar organic solvent.

In another aspect, the present invention provides a nutritional supplement, the nutritional supplement including an antioxidant composition produced by the above-described method. Preferably, the antioxidant composition is a solid composition. In this aspect, the nutritional supplement can be provided in any convenient form, such as a powder, a tablet or a capsule. Most preferably, the nutritional supplement is in the form of a tablet or a capsule. The nutritional supplement could, however, be provided in a liquid form, such as in a drink. If provided as a drink, it is convenient to use a polar organic solvent such as food-grade ethanol or an aqueous mixture thereof. The methods of preparing any of these dosage forms are well known to those skilled in the art.

In another embodiment, the present invention provides a method of preparing an antioxidant composition from wastewater produced as a by-product of olive oil production. In this embodiment, the method includes the steps of providing an aqueous starting material, the starting material being wastewater from olive oil production, passing the aqueous starting material through a solid matrix to trap antioxidant components in the wastewater on the matrix, and washing the matrix with a polar organic solvent to remove the antioxidant components trapped thereon, to obtain a solution of the antioxidant composition in the polar organic solvent.

As discussed above, one step of the conventional olive oil production process includes making a slurry of olive solids, olive oil, and water. The water and olive oil are pressed out of the slurry and separated, then the oil is separated from the water by decantation or centrifugation. This "water", referred to herein as "wastewater", is actually a solution of water-soluble antioxidant components, possibly along with small amounts of other materials left over from the olive oil manufacturing process. In this embodiment, this wastewater is used as the starting material in a method of preparing an antioxidant composition. Thus, it is a particular advantage of this embodiment of the present invention that wastewater which is an unwanted by-product of the olive oil manufacturing process can be productively used.

Once the wastewater is provided, the wastewater can be treated in the same fashion as the aqueous phase as described above. Thus, the wastewater is passed through a solid matrix to trap at least a portion of the antioxidants contained therein on the matrix, and the matrix is washed with a polar organic solvent to remove the antioxidant components, forming a solution of the antioxidant composition in the polar organic solvent. As above, the polar organic solvent can be partially removed to form a liquid concentrate, or preferably substantially completely removed to produce a solid antioxidant composition. The optional step of treatment by acid can also be used, either by acidifying the wastewater starting material, by acidifying the solution of the antioxidant composition in the polar organic solvent, or by dissolving the solid antioxidant composition in an acid, and preferably removing, i.e., re-drying, the antioxidant composition.

In another embodiment, the present invention provides a method of increasing the antioxidant activity of a product. In this embodiment, the method includes the steps of providing an antioxidant composition derived from olives, olive pulp, olive oil or wastewater from olive oil manufacturing, and combining the antioxidant composition with a product to form a product having enhanced antioxidant activity. The step of providing an antioxidant composition can be carried out by any of the methods described above.

In this embodiment, the product before combining with the antioxidant composition can be any product subject to unwanted oxidation, or any composition intended itself to have antioxidant properties. Thus, the product can be a food product subject to oxidation, or an oil, such as an edible oil or a cooking oil. Alternatively, the product can be a cosmetic, a topical antioxidant composition, a preservative composition, or a nutritional supplement. By the method of the present invention, the antioxidant composition imparts to the product an antioxidant activity, or enhances any antioxidant activity already present.

EXAMPLES

Example 1

Antioxidant Composition from Green Olives

A sample of commercial, bottled green olives (207.43 g) was chopped in a food processor then extracted with water (300 mL) at a reflux temperature for 1 hour. The aqueous phase was separated from the solids by filtration and retained. The solid material was further washed with hot water, and the aqueous filtrate added to the retained aqueous phase. The aqueous phase was allowed to cool, then passed through a column of Amberlite® XAD-16 resin (Rohm Haas) at a rate of approximately 5 mL/min. After all of the aqueous phase had been passed through the column, the column was washed with 100 mL of fresh water. Methanol (250 mL) wash then passed through the column, and the effluent was collected. Evaporation of the methanol at reduced pressure gave a tan solid weighing 0.5 1 g.

Example 2

Antioxidant Composition from Black Olives

Fresh black (ripe) olives were collected from a tree growing in Sunnyvale, Calif. The olive fruit was separated from the pits, and a total of 397.8 g of the fruit was extracted with water (550 mL) at a reflux temperature for 1 hour. The aqueous phase was separated from the solids by filtration and retained. The solid material was further washed with hot water, and the filtrate added to the aqueous phase. The aqueous phase was allowed to cool, then passed through a column of Amberliteg XAD-16 resin (Rohm Haas) at a rate of approximately 10 mL/min. After all of the aqueous phase had been passed through the column, the column was washed with 200 mL of fresh water. Methanol was then passed through the column, and about 400 mL of the effluent was collected. Evaporation of the methanol at reduced pressure gave a tan solid 13.91 g.

Example 3

Antioxidant Composition from Olive Pulp I

Olive pulp from olive oil production was obtained from a commercial supplier. The pulp was air dried until the water content reached about 11% by weight. A portion of the pulp (138.94 g) was extracted with 350 mL of water at a reflux temperature for 1 hour. The extraction mixture was filtered, and the aqueous filtrate was passed through a column filled with Amberlite(® XAD-16HP resin (Rohm Haas) at 5 mL/min. After loading, the column was rinsed with 125 mL water, and then with methanol, collecting about 160 mL of the methanol effluent. After removal of the solvent at reduced pressure, 0.71 g of solid was obtained.

Example 4

Antioxidant Composition from Olive Pulp II

An olive pulp (or "mash") was obtained from a commercial supplier and air dried until the water content reached about 11% by weight. A 148.48 g sample of the mash was extracted with water (300 mL) at a reflux temperature for 1 hour. The mixture was filtered, washed with hot water, and loaded onto an Amberlite® XAD-7 column (Rohm Haas). The column was washed with methanol, and the methanol fraction (200 mL) was cooled in a freezer overnight. The solid material (0.54 g) that formed in the methanol was removed by filtration, and the methanol was evaporated to yield 5.21 g of a solid composition.

Example 5

Antioxidant Composition from Wastewater

Wastewater from olive oil production was obtained from a commercial supplier. A 250 ml sample of this water was first filtered, and then passed through an Amberlite® XAD-16HP column (Rohm Haas) at 5 mL/min. After the water had been added to the column, another 135 mL (1 bed volume) of a fresh water wash was passed through the column. Next, methanol was passed through the column, and about 90 mL of the methanol effluent wash collected. The methanol was evaporated to give 0.35 g of solid.

Example 6

Methods of Analysis

To characterize the compositions of the present invention, several methods were used to measure the total amount of phenolic components in the compositions, and the antioxidant activity of the compositions. The methods used were as follows.

A. Total Phenols Assay

The method of Singleton (Singleton, V. L., Rossi, J. A. Jr., "Colorimetery of total phenolics with phosphomolybdic-phosphotungstic acid reagent", *Am. J Enol. Vitig.*, 1965; 16: 144–158) was used, with some modification, to determine the total phenolic content of compositions of the present invention. The method is as follows: A stock solution of a solid composition according to the present invention in 50% aqueous ethanol is prepared. The stock solution is diluted with water to a concentration of about 200 to 250 µg/mL. Next, 20 µL of this solution is placed into each of three wells of a flat bottom ELISA plate. 100 µL of 0.1N Folin-Ciocalteu reagent (Sigma, diluted) is added to each of the same wells. After 0.5 to 5 minutes, 80 µL of aqueous sodium carbonate (75 g/L) is added to each well. The plate is incubated at room temperature for two hours. The optical density at 750 nm ($OD_{750}$) is measured. A 6 point calibration solution is run simultaneously according to the above protocol, where 20 µL of a solution of gallic acid with a concentration of 0 to 100 µg/mL is used. Using this assay, the total phenol content of the sample is expressed as an equivalent weight percent of gallic acid.

B. Antioxidant Activity by Photochemiluminescence Assay

The method of Popov (Popov I. N., Lewin G., "Photochemiluminescent detection of antiradical activity; IV: Testing of lipid-soluble antioxidants", *J. Biochemical and Biophysical Methods* 1996; 31: 1–8) was used, with some modification, to determine the antioxidant activity of compositions of the present invention. The method is as follows: 2.4 mL of methanol is mixed with 0.1 mL of 0.1 M carbonate buffer (pH 10.5) in a 5 mL glass test tube. Then 30 µL of a 30 µM solution of luminol is added. Finally, 10–50 µL of sample solution (50% solution of the composition in ethanol) is added. The test tube is placed in a photochemiluminometer (PHOTOCHEM, FAT, GmbH, Germany) and the integral of the luminescence curve is recorded. A calibration table was built using Trolox, or d-α-tocopherol (0.1–3 nM), as a standard. In this method, the antioxidant activity is expressed as an equivalent concentration of Trolox, or d-α-tocopherol.

C. Antioxidant Activity by LDL Oxidation Assay

Figure 1B:
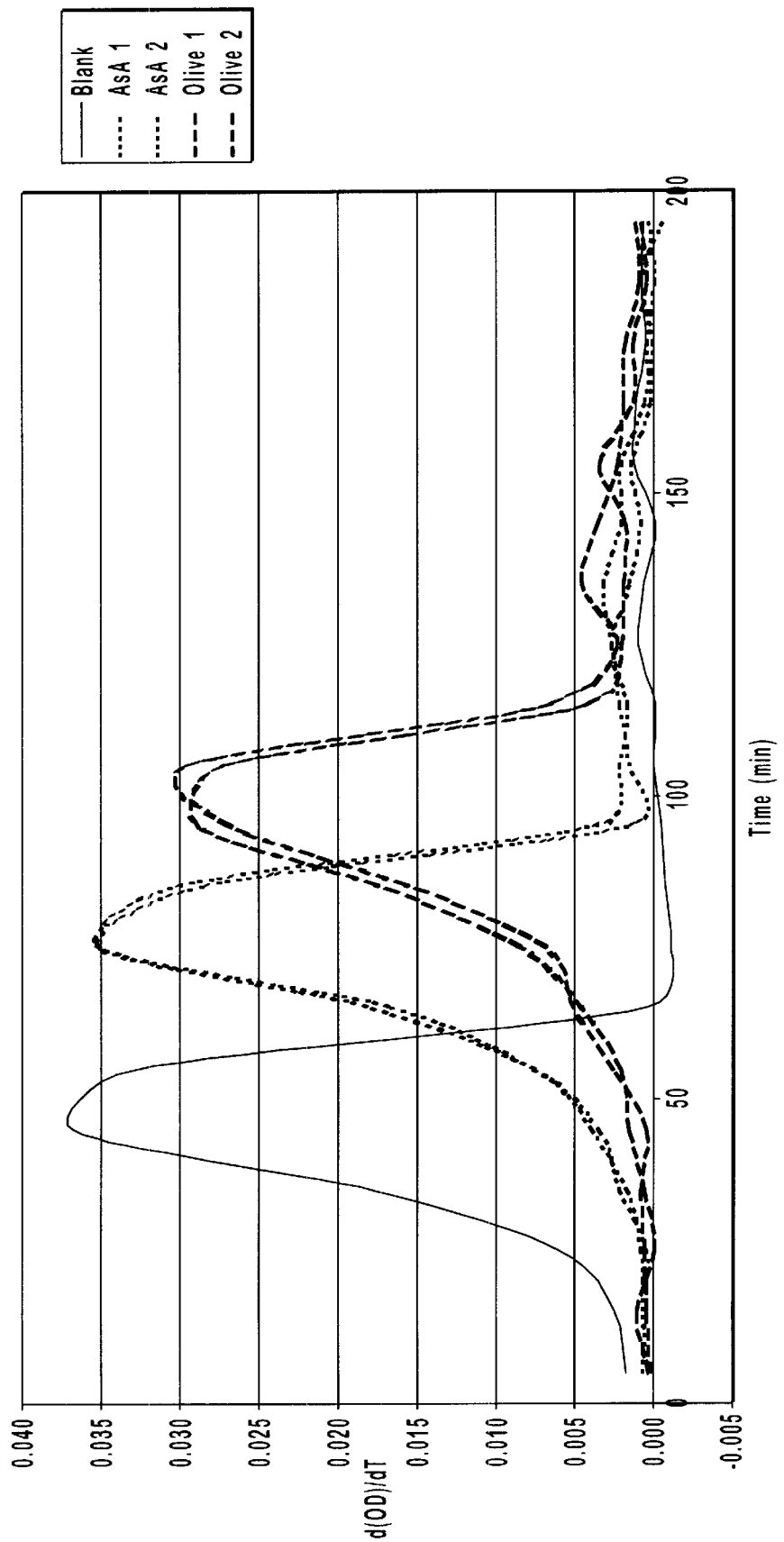
FIG. 1B is a plot of the first derivative of optical density versus time from FIG. 1A, and is used to calculate the lag time of LDL oxidation. The antioxidant activity of the compositions of the present invention is calculated by the increase in lag time of LDL oxidation.

The method of Esterbauer (Esterbauer, H., Striegl, G., Puhl, H., Rotheneder, M., "Continuous monitoring of in vitro oxidation of human low density lipoprotein", *Free Radic. Res. Commun*, 1989; 6(1): 67–75) was used, with some modification. The method is as follows: The sample to be measured is dissolved in a phosphate buffer solution (PBS, 0.15 M NaCl–0.05 M Na Phosphate Buffer—pH 7.4). The exact concentration is noted (approximately 30–60 µg/mL of extract to be measured). To 100 µL of this solution is added to 900 µL of an oxidizing buffer (made from human LDL (120 µL of 5 mg/mL solution with d=1.019–1.063 g/mL, purchased from PerImmune, Rockville, Md.) and copper sulfate (20 µL of 10 mM aqueous solution) in 8 mL PBS). A blank sample made with 100 µL PBS and 900 µL oxidizing buffer is also prepared. Each solution is then transferred to a 1 cm quartz cuvette, and the cuvette is placed into thermostat (37° C.). ArA HP-8452A Diode Array Spectrophotometer measures optical density at 234 nm ($OD_{234}$), making a measurement every 5 minutes. The lag time ($T_{lag}$) for oxidation is calculated as the maximum of the first derivative of the optical density curve. A standard containing ascorbic acid (~10 µM) is run with each assay. Final results are reported as ascorbic acid equivalents (AsA eq.), calculated from the lag time according to the Esterbauer reference. FIG. 1A shows the optical density versus time for the blank control sample, and duplicate measurements with the ascorbic acid standard and an antioxidant composition of the present invention, and FIG. 1B shows the corresponding first derivative curves.

Example 7

Assay of Compositions from Examples 1–5

The compositions obtained in Examples 1–5 were assayed for total phenol content and antioxidant activity. The antioxidant assay was carried out using the LDL oxidation assay procedure described in Example 6C. The results of the assays are presented in Table 1.

TABLE 1

| | Composition Assays | |
|---|---|---|
| Sample (source) | Phenols (wt % gallic acid equiv.) | Antioxidant Activity (ascorbic acid equiv.) |
| Example 1 (green olives) | 27.6 | 0.74 |
| Example 2 (ripe olives) | 24.4 | 0.58 |
| Example 3 (olive pulp) | 19.0 | 0.62 |
| Example 4 (olive pulp) | 16.4 | 0.61 |
| Example 5 (wastewater) | 16.8 | 0.47 |

Example 8

HPLC Characterization

The extract from Example 4 was examined by HPLC to characterize the components of the composition. The HPLC parameters were as follows:

Column: Phenomenex C-18, 5µ, 150×4.6 mm, with a Phenomenex security guard column Column temperature: 35° C.

Injection volume: 20 µL

Mobile phase A: 0.05 M phosphate buffer, pH 3.0
Mobile phase B: 30/10/60 (v/v/v) mixture of 0.1 M phosphate buffer (pH 3.0), methanol, and acetonitrile
Gradient:
    0–10 min 6% B isocratic
    10–40 mm linear gradient 6% B to 30% B
    40–50 min linear gradient 30% B to 100% B
    50–65 min isocratic 100% B
System: CoulArray HPLC System model no. 5600 from ESA, Chelmford, Mass., with 16 channel coulometric electrode array detector, modified to use an HP 1050 wavelength UV detector in place of the 16$^{th}$ channel, auto sampler, thermostated column, inline vacuum degasser, Pentium processor, and CoulArray 5600 software
Cell potentials: 0, 60, 120, 180, 240, 300, 360, 420, 480, 540, 600, 660 mV
Wavelength: UV 280 nm.

Figure 2:
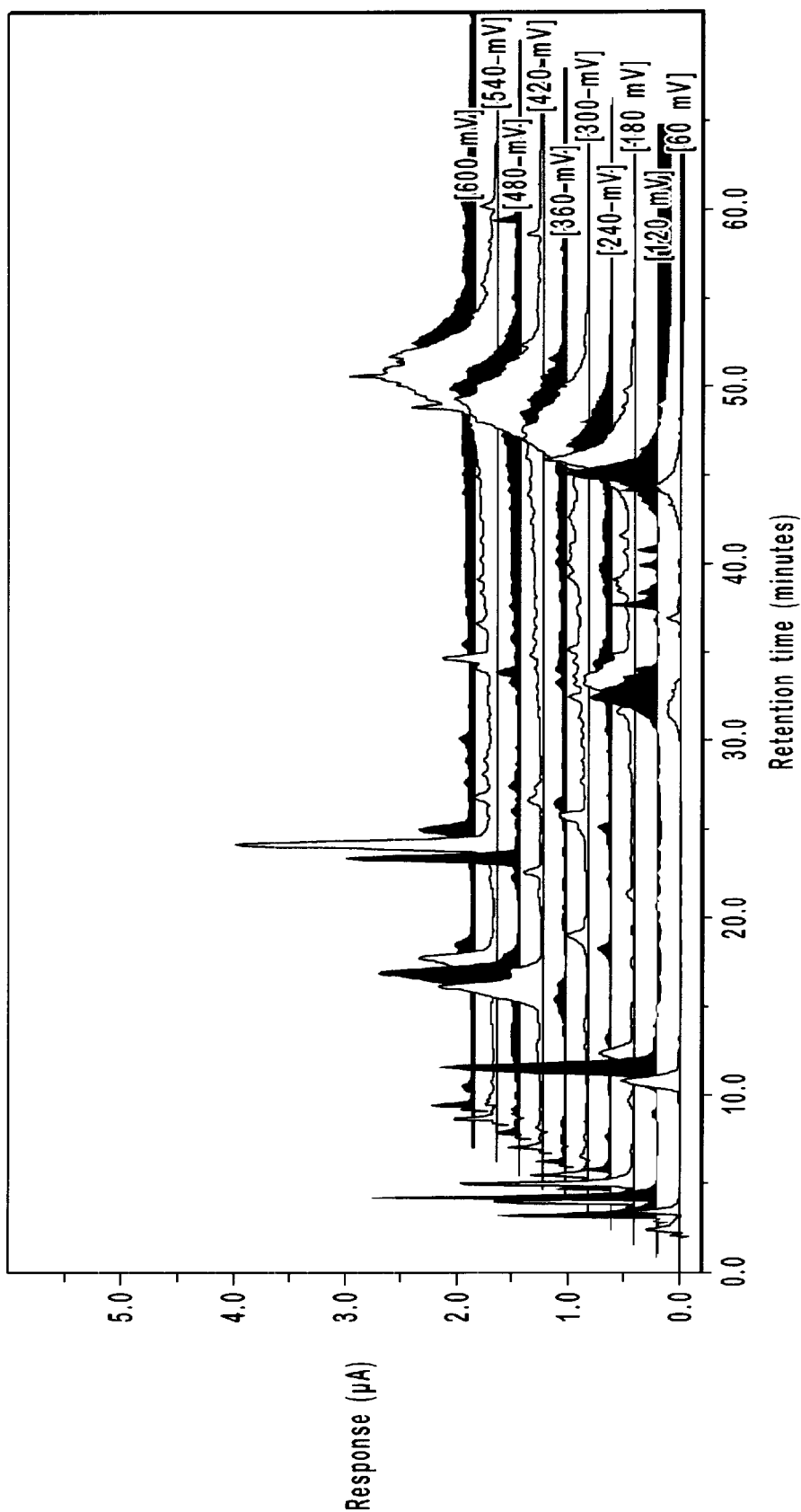
FIG. 2 shows a three-dimensional HPLC chromatogram of an antioxidant composition of the present invention described in Example 4.
Figure 3:
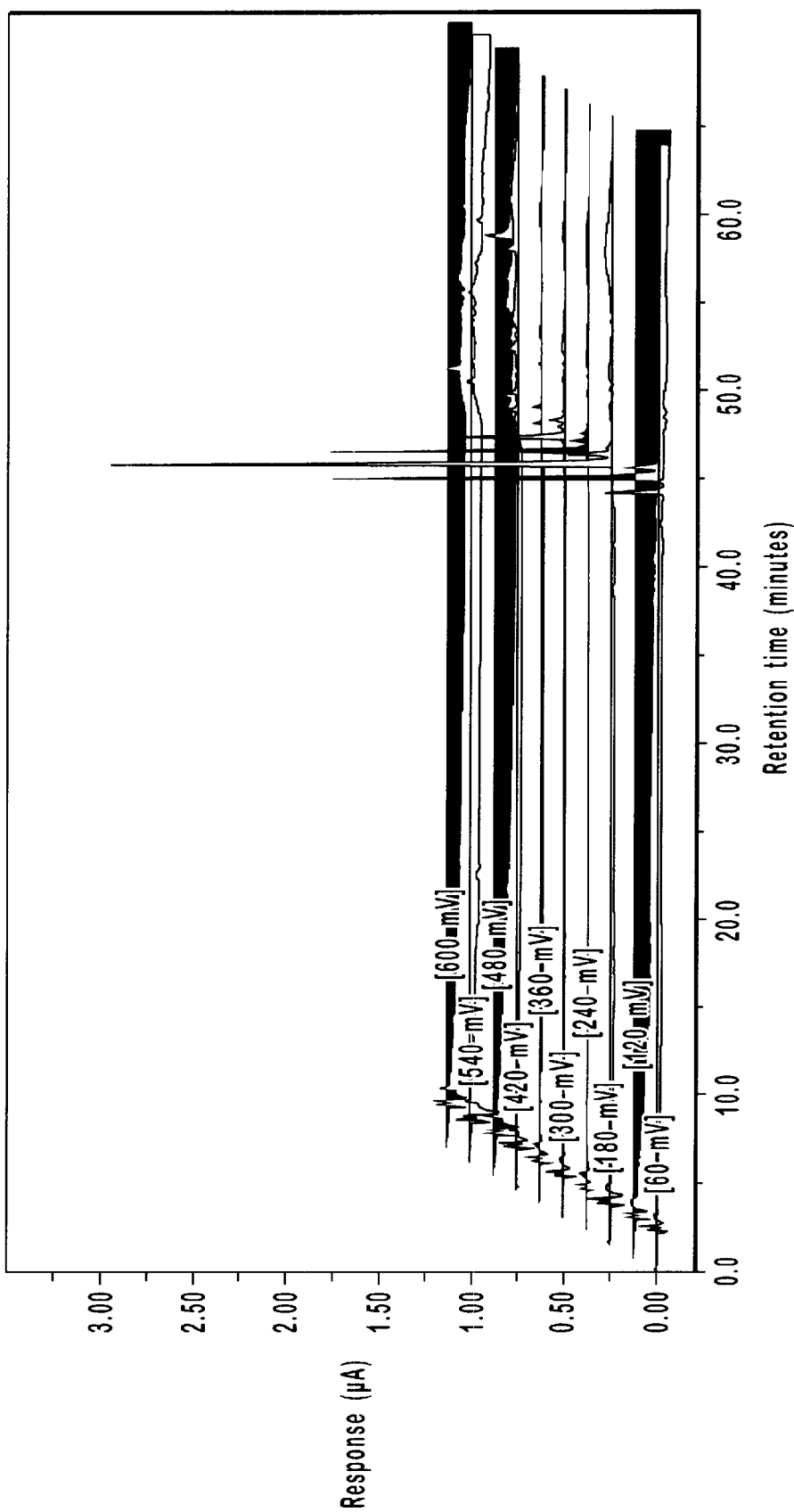
FIG. 3 shows a three-dimensional HPLC chromatogram of oleuropein used in identifying components of the antioxidant compositions of the present invention.
Figure 4:
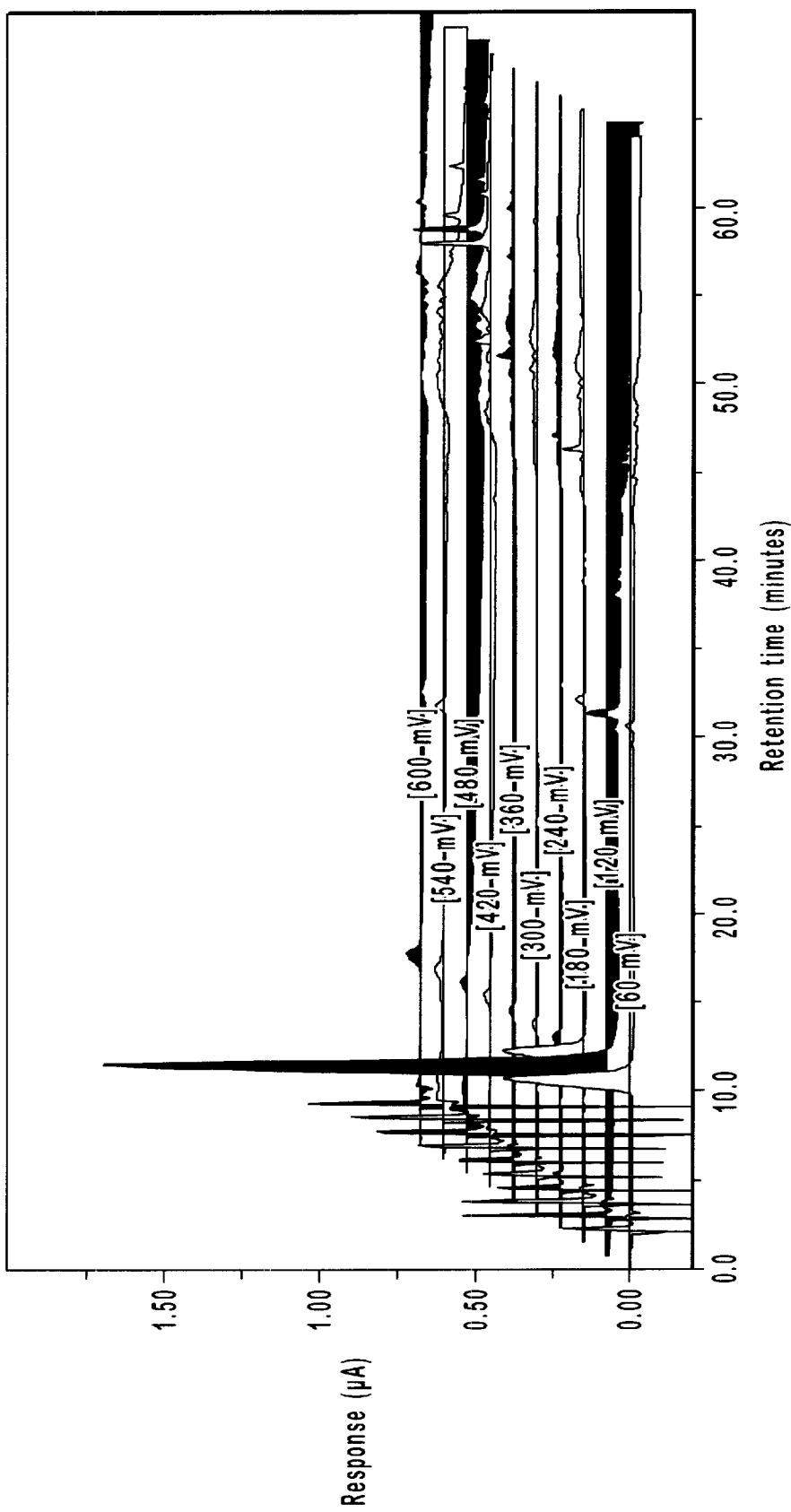
FIG. 4 shows a three-dimensional HPLC chromatogram of hydroxytyrosol used in identifying components of the antioxidant compositions of the present invention.

The chromatogram of the Example 4 sample is shown in FIG. 2. The identity of two major peaks was established by comparing retention times and electronic response ratios of authentic samples with the chromatogram of FIG. 2. Co-injections of tyrosol (Aldrich Chemicals) and hydroxytyrosol with the extract comfirmed these assignments. Hydroxytyrosol was obtained by hydrolysis of oleuropein (Fleming H P, Walter W M, Etchells J L, "Antimicrobial properties of Oleuropein and products of its hydrolysis from green olives"*App. Microbio* 1973; 26: 777–782). Oleuropein was also identified in the extract mixture, although it is not clearly separated from other components at a retention time of 44 minutes. Chromatograms of oleuropein and hydroxytyrosol are shown in FIGS. 3 and 4, respectively.

Example 9

Total Carbohydrate Characterization

The extract from Example 4 was assayed for total carbohydrates by the method of Dubois (Dubois, M., Gilles, K. A., Hamilton, J. K., Rebers, P. A., Smith, F., "Colorimetric Method for Determination of Sugars and Related Substances", Analytical *Chemistry,* 1956; 28: 350–356.). A solution of the olive extract of Example 4 in a 50/50 (v/v) water/ethanol solution was diluted volumetrically with water to a final concentration of 64.8 µg/mL. A second sample with a concentration of 86.0 µg/mL was also prepared. 500 µL of each solution was mixed with 500 L of a 5% phenol-water solution. Concentrated sulfiric acid (2.5 mL) was added, and the tube was mixed well. The tube was then incubated at room temperature for 0.5 hour. Optical density at 490 nm was measured on a Spectromax-340 ELISA plate reader. Calibration samples were prepared with glucose (5 point calibration at 0, 31.4, 47.1, 62.8 and 78.5 µg/mL).

The total carbohydrate content found, in units of glucose equivalent weight %, was 32.0 and 31.0% for the two samples, respectively. Oleuropein, 4-hydroxybenzoic acid, tyrosol, 3,4-dihydroxycinnamic acid and 4-hydroxy-3-methoxybenzoic acid all in concentrations of 100 µg/mL were also run in this assay. Only Oleuropein showed a positive result, with a total carbohydrate concentration of 34.0% (theoretical calc.=34.1%). All other compounds gave 0%.

Example 10

Antioxidant Activity by Photochemiluminescence

The antioxidant activity of the extract of Example 4 was measured, using the photochemiluminescence assay described in Example 6B. Four measurements were made, and the results averaged, to give an average antioxidant activity of 7.64 mM trolox equivalents per gram. For comparison, the measurement was also carried out on a commercially available sample of grape seed extract (Indena), which gave an antioxidant activity of 14.56 mM trolox equivalents per gram.

Example 11

Acid-Treated Composition

The extract from Example 4 (100 mg) was dissolved in 25 mL of 80% aq. methanol. 3 mL of this solution was mixed with 3 mL of HCl in methanol (from 15 mL conc. HCl and 85 mL methanol). The solution was then heated to 85° C. for 1 hour. The solution was then cooled and the composition characterized. Antioxidant activity was measured both by the photochemiluminescence assay of Example 6B and by the LDL oxidation assay of Example 6C. Total phenol content was measured by the method of Example 6A.

Figure 5:
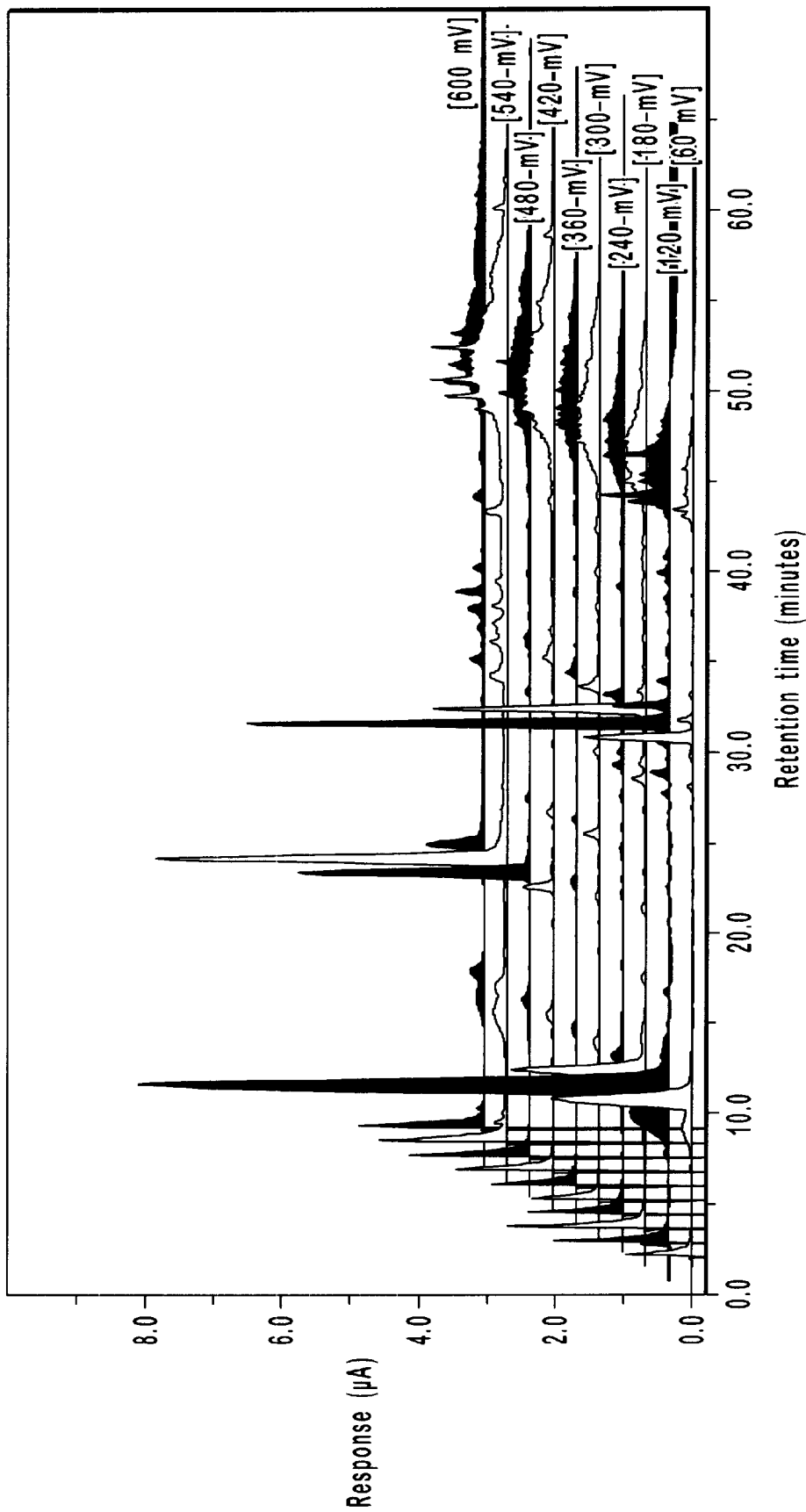
FIG. 5 shows a three-dimensional HPLC chromatogram of an antioxidant composition of the present invention after treatment with acid.

In addition, an HPLC of the acid-treated extract was also run, under the conditions described above in Example 8. The chromatogram is shown in FIG. 5. The acid treatment reduces the size of the peaks at retention times 40–46 minutes, and removes the peak at the high potential channels with retention time of 11 minutes. The amount of hydroxytyrosol at 10.9 minutes and tyrosol at 18 minutes is increased, and a new peak at a retention time of 31 minutes was observed. The amounts of hydroxytyrosol, tyrosol and oleuropein were estimated by comparison of peak areas with standards.

The results of all of these assays are shown in Table 2. For comparison, the corresponding values for the Example 4 composition are shown.

TABLE 2

Assay of Acid-Treated Composition

| Assay | Example 4 | Example 11 |
|---|---|---|
| Antioxidant Activity (mM trolox eq./g) | 7.64 | 18.34 |
| Antioxidant Activity (AsA equiv.) | 0.61 | 1.12 |
| Phenols (wt % gallic acid eq.) | 16.4 | 19.8 |
| Hydroxytyrosol (wt. %) | 1.09 | 3.99 |
| Tyrosol (wt. %) | 0.5 | 1.10 |
| Oleuropein (wt. %) | 0.4 | 0.09 |

Example 12

Antioxidant Composition Under Acidic Conditions

The effect of acidic conditions on the extraction process was investigated by comparing aqueous extraction with an acidic aqueous extraction. Olive pulp (Vemi Olive Oil Co.) was split into two batches. 87.6 g was extracted with water (250 mL at reflux for 1 hr). A second batch of 87.8 g was extracted with 250 mL of 0.5M HCl (prepared from 12.5 mL conc. HCl and 237.5 mL water) at reflux for 1 hr. Both materials were handled in the same manner for the remainder of the experiment as follows. The solids were removed from the extraction solvent by filtration, and the cake was washed with hot water. After cooling, the filtrate was loaded onto a 150 mL XAD-7 column at a flow rate of 5 mL per minute. After all of the filtrate was added to the column, an additional 50 mL clean water was passed through the column. Next the column was washed with methanol. The methanol fraction (200 mL) was stripped to give solids. The two samples were assayed, and the results are presented in Table 3.

TABLE 3

Effect of Acidic Extraction Conditions

| Assay | Aqueous Extraction | Acidic Aqueous Extraction |
|---|---|---|
| Yield | 0.80 g | 1.71 g |
| Phenols (wt % gallic acid eq.) | 13.8 | 14.7 |
| Antioxidant Activity (AsA equiv.) | 0.46 | 0.57 |

Example 13

Enhancement of Antioxidant Activity in an Oil

The extract of Example 4 was dissolved in a 50/50 (v/v) water/ethanol mixture, with a concentration of 4.34 mg/mL. This solution was mixed with an equal volume of acetic acid. 1 mL of the resultant mixture was then added to 30 mL of vegetable oil (Wesson). The mixture was shaken for 30 minutes, giving a stable emulsion. A control sample was prepared, using the same amounts of acetic acid, water and ethanol, but without the antioxidant composition, and 1 mL of the control was added to 30 mL vegetable oil. 1 mL of each emulsion was then extracted with 0.5 mL methanol. The methanol layer was separated, diluted 1/10 (v/v) with methanol, and the antioxidant activity was measured by the photochemilumenesence assay of Example 6B. The control sample showed an antioxidant activity of 0.18 mM trolox equivalent per gram, whereas the sample containing the antioxidant extract of the present invention showed approximately three times the antioxidant activity, 0.53 mM trolox equivalent per gram.

Example 14

Enhancement of Antioxidant Activity in Cosmetics

The extract from Example 4 was dissolved in a 50/50 (v/v) water/ethanol mixture to a concentration of 2.34 mg/mL. 25 µL of the solution was added to each of three cosmetic products: (1) Aveeno moisturizing lotion (Ryoelle Laboratories, Division of S. C. Johnson & Son, Inc., Racine, Wis.) 0.80 g; (2) Yves Rocher—Revitalizing Cream for Hands (Soin Beaue Des Mains, La gacilly, France) 0.76 g; and (3) USANA Hand and body lotion (USANA Inc., Salt Lake City, Utah) 0.98 g. Each was mixed well, and no visible changes to the cosmetic composition were observed. Each was allowed to stand for 30 minutes, then each starting cosmetic and antioxidant-enhanced mixture was assayed for antioxidant activity by the photochemilumenesence assay of Example 6B. The results are shown in Table 4.

TABLE 4

Antioxidant Enhancement of Cosmetics (AsA equivalents)

Antioxidant Activity (AsA equivalents)

| Cosmetic Product | Starting Cosmetic | Enhanced Cosmetic | % Increase |
|---|---|---|---|
| Aveeno | 1.27 | 3.08 | 143% |
| Yves Rocher | 0.94 | 3.71 | 295% |
| USANA | 0.57 | 2.07 | 263% |

The data in the Table show that the antioxidant composition of Example 4 increases the antioxidant activity of cosmetic products by as much as nearly 300%.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of preparing an antioxidant composition, the method comprising the steps of:
    (a) providing a starting material comprising olive pulp by-product of olive oil production;
    (b) extracting the starting material with a polar aqueous solvent to form an aqueous phase containing antioxidant components;
    (c) passing the aqueous phase through a macroreticulated crosslinked polymeric resin to trap at least a portion of the antioxidant components on the polymeric resin; and
    (d) washing the polymeric resin with a polar organic solvent to remove at least a portion of the antioxidants components trapped thereon, to obtain a solution of the antioxidant composition in the polar organic solvent.

2. The method of claim 1, wherein the polar aqueous solvent comprises water or a mixture of water and a water-miscible polar organic solvent.

3. The method of claim 2, wherein the water-miscible polar organic solvent is selected from the group consisting of $C_1$ to $C_4$ alcohols, esters, amides, ethers, nitrites, ketones, and mixtures thereof.

4. The method of claim 1, wherein the polar aqueous solvent is a mixture of water and methanol, ethanol, acetonitrile, or acetone.

5. The method of claim 1, wherein the antioxidant components comprise phenolic antioxidant compounds.

6. The method of claim 1, wherein the step of extracting is carried out at a temperature from about 20° C. to the reflux temperature of the polar aqueous solvent.

7. The method of claim 1, wherein the polar aqueous solvent further comprises a water-soluble acid in an amount such that the polar aqueous solvent has an acidic pH.

8. The method of claim 7, wherein the acidic pH is from about 0 to about 4.

9. The method of claim 7, wherein the acidic pH is from about 1 to about 3.

10. The method of claim 1, wherein the polymeric resin is a styrenic resin, an acrylic resin, or a phenolic resin.

11. The method of claim 1, wherein the polar organic solvent in step (d) is selected from the group consisting of $C_1$ to $C_4$ alcohols, acetone, ethyl acetate, acetonitrile, dioxane, aqueous mixtures thereof, and mixtures thereof.

12. The method of claim 1, wherein the polar organic solvent in step (d) is methanol, ethanol, acetone, ethyl acetate, aqueous mixtures thereof, or a mixture thereof.

13. The method of claim 1, further comprising the step of evaporating a portion of the polar organic solvent to form a liquid concentrate of the antioxidant composition.

14. The method of claim 1, further comprising the step of evaporating substantially all of the polar organic solvent to form a solid antioxidant composition.

15. The method of claim 1, further comprising the step of adding to the solution of the antioxidant composition in the polar organic solvent an amount of an acid miscible in the solution sufficient to give the solution a pH of about 0 to about 4.

16. The method of claim 14, further comprising treating the solid antioxidant composition with an acidic aqueous solution having a pH of about 0 to about 4.

17. The method of claim 10, further comprising evaporating substantially all of the acidic aqueous solution.

18. An antioxidant composition produced by the method of claim 1.

19. An antioxidant composition produced by the method of claim 13.

20. An antioxidant composition produced by the method of claim 14.

21. A nutritional supplement comprising the antioxidant composition of claim 9.

22. A nutritional supplement comprising the antioxidant composition of claim 20.

23. The nutritional supplement of claim 22 in the form of a powder, a drink solution, a tablet, or a capsule.

24. A method of preparing an antioxidant composition, the method comprising the steps of:
  (a) providing a starting material comprising olive pulp by-product of olive oil production;
  (b) extracting the starting material with a polar aqueous solvent to form an aqueous phase containing antioxidant components, the polar aqueous solvent including a water-soluble acid in an amount such that the polar aqueous solvent has an acidic pH;
  (c) passing the aqueous phase through a macroreticulated crosslinked polymeric resin to trap at least a portion of the antioxidant components on the polymeric resin; and
  (d) washing the polymeric resin with a polar organic solvent to remove at least a portion of the antioxidant components trapped thereon, to obtain a solution of the antioxidant composition in the polar organic solvent.

25. The method of claim 24, wherein the polar aqueous solvent comprises water or a mixture of water and a water-miscible polar organic solvent.

26. The method of claim 25, wherein the water-miscible polar organic solvent is selected from the group consisting of $C_1$ to $C_4$ alcohols, esters, amides, ethers, nitrites, ketones, and mixtures thereof.

27. The method of claim 24, wherein the polar aqueous solvent is a mixture of water and methanol, ethanol, acetonitrile, or acetone.

28. The method of claim 24, wherein the antioxidant components comprise phenolic antioxidant compounds.

29. The method of claim 24, wherein the step of extracting is carried out at a temperature from about 20° C. to the reflux temperature of the polar aqueous solvent.

30. The method of claim 24, wherein the acidic pH is from about 0 to about 4.

31. The method of claim 24, wherein the acidic pH is from about 1 to about 3.

32. The method of claim 24, wherein the acid includes at least one acid selected from the group consisting of hydrochloric acid, sulfuric acid, and phosphoric acid.

33. The method of claim 24, wherein the polymeric resin is a styrenic resin, an acrylic resin, or a phenolic resin.

34. The method of claim 24, wherein the polar organic solvent in step (d) is selected from the group consisting of $C_1$ to $C_4$ alcohols, acetone, ethyl acetate, acetonitrile, dioxane, aqueous mixtures thereof, and mixtures thereof.

35. The method of claim 24, wherein the polar organic solvent in step (d) is methanol, ethanol, acetone, ethyl acetate, aqueous mixtures thereof, or a mixture thereof.

36. The method of claim 24, further comprising the step of evaporating a portion of the polar organic solvent to form a liquid concentrate of the antioxidant composition.

37. The method of claim 24, further comprising the step of evaporating substantially all of the polar organic solvent to form a solid antioxidant composition.

38. An antioxidant composition produced by the method of claim 24.

39. An antioxidant composition produced by the method of claim 36.

40. An antioxidant composition produced by the method of claim 37.

41. A nutritional supplement comprising the antioxidant composition of claim 39.

42. A nutritional supplement comprising the antioxidant composition of claim 40.

* * * * *

UNITED STATES PATENT AND TRADEMARK OFFICE
CERTIFICATE OF CORRECTION

PATENT NO.    : 6,358,542 B2
DATED         : March 19, 2002
INVENTOR(S)   : John Cuomo and Alexandre B. Rabovskiy It is certified that error appears in the above-identified patent and that said Letters Patent is hereby corrected as shown below:

<u>Title page,</u>
Item [56], References Cited, OTHER PUBLICATIONS,
After "Rimm," change "Dimitros" to -- Dimitrios --
After "Helsing, and" change "Dimitros" to -- Dimitrios --
After "Nardini," change "M.D' Aquino," to -- M. D'Aquino, --
After "Res." change "Commms.," to -- Comms., --
After "Actions of" change "Thymiol," to -- Thymol --

<u>Column 6,</u>
Line 17, after ""cake"" delete "0"
Line 21, after ""pulp"" delete "0"

<u>Column 8,</u>
Line 1, after "AMBERLITE®" delete "0"
Line 21, after "thereof" insert a period <u>Column 10,</u>
Line 23, after "weighing" change "0.5 1 g." to -- 0.51 g. --
Line 37, after "column of" change "Amberliteg" to -- Amberlite® --
Line 54, before "XAD-16HP" change "Amberlite(®" to -- Amberlite® --

<u>Column 11,</u>
Line 29 and 53, after "Assay" insert a colon

<u>Column 12,</u>
Line 4, after "Assay" insert a colon
Line 22, before "HP-8452A" change "ArA" to -- An --

<u>Column 13,</u>
Line 6, after "10-40" change "mm" to -- min --
Line 27, after "(Fleming" change "H P," to -- HP, --
Line 27, after "Walter" change "W M," to -- WM, --
Line 27, after "Etchells" change "J L," to -- JL, --
Line 39, after "Hamilton," change "J. K.," to -- J.K., --
Line 39, after "Rebers," change "P. A.," to -- P.A., --
Line 46, after "500" change "L" to -- $\mu$L --

<u>Column 14,</u>
Line 59, after "pulp" change "(Vemi" to -- (Verni --

<u>Column 16,</u>
Line 53, after "20º C" delete the period

UNITED STATES PATENT AND TRADEMARK OFFICE
CERTIFICATE OF CORRECTION

PATENT NO. : 6,358,542 B2
DATED : March 19, 2002
INVENTOR(S) : John Cuomo and Alexandre B. Rabovskiy It is certified that error appears in the above-identified patent and that said Letters Patent is hereby corrected as shown below:

Column 17,
Line 18, after "claim" change "10," to -- 16, --
Line 27, after "claim" change "9." to -- 19. --

Column 18,
Line 13, after "20° C" delete the period
Line 47, insert -- The nutritional supplement of claim 42 in a form selected from the group consisting of a powder, a drink solution, a tablet, and a capsule. --

Signed and Sealed this

Twelfth Day of November, 2002

*Attest:*

*Attesting Officer*

JAMES E. ROGAN
*Director of the United States Patent and Trademark Office*